United States Patent
Schank, Jr. et al.

(10) Patent No.: US 12,024,431 B2
(45) Date of Patent: Jul. 2, 2024

(54) SYSTEM AND METHODS FOR THE PRODUCTION OF HYDROGEN GAS

(71) Applicants: William H. Schank, Jr., Howell, MI (US); Steven C. Cardona, Driftwood, TX (US)

(72) Inventors: William H. Schank, Jr., Howell, MI (US); Steven C. Cardona, Driftwood, TX (US)

(*) Notice: Subject to any disclaimer, the term of this patent is extended or adjusted under 35 U.S.C. 154(b) by 869 days.

(21) Appl. No.: 16/620,654

(22) PCT Filed: Jun. 12, 2018

(86) PCT No.: PCT/US2018/037167
§ 371 (c)(1),
(2) Date: Dec. 9, 2019

(87) PCT Pub. No.: WO2018/231876
PCT Pub. Date: Dec. 20, 2018

(65) Prior Publication Data
US 2020/0180956 A1 Jun. 11, 2020

Related U.S. Application Data

(60) Provisional application No. 62/518,771, filed on Jun. 13, 2017.

(51) Int. Cl.
*C01B 3/54* (2006.01)
*B01D 33/56* (2006.01)
(Continued)

(52) U.S. Cl.
CPC .............. *C01B 3/54* (2013.01); *B01D 33/56* (2013.01); *B01D 61/025* (2013.01);
(Continued)

(58) Field of Classification Search
CPC ............ C01B 3/54; C01B 2203/04435; B01D 61/025; B01D 61/027; B01D 61/145; B01D 61/422; B01D 2257/60
(Continued)

(56) References Cited

U.S. PATENT DOCUMENTS

2007/0184309 A1 8/2007 Gust
2008/0311640 A1* 12/2008 Cox .................. C12M 29/20
435/303.2
(Continued)

OTHER PUBLICATIONS

The role of pH control on biohydrogen production by single stage hybrid dark- and photo-fermentation R. Zagrodnik et al Bioresource Technology, v 194, pp. 187-195 (Year: 2015).*
(Continued)

*Primary Examiner* — Coris Fung
*Assistant Examiner* — Keling Zhang
(74) *Attorney, Agent, or Firm* — BROOKS KUSHMAN P.C.

(57) ABSTRACT

Methods and systems are disclosed for using industrial waste for the production of hydrogen gas. The method includes examining a ph level of the industrial waste, removing contaminate from the industrial waste, conditioning and concentrating the industrial waste to a proton-rich solution, and using the resulting proton-rich solution as the proton source in a hydrogenase catalyzed hydrogen production system.

18 Claims, 2 Drawing Sheets

(51) Int. Cl.
*B01D 61/02* (2006.01)
*B01D 61/14* (2006.01)
*B01D 61/42* (2006.01)

(52) U.S. Cl.
CPC ......... *B01D 61/027* (2013.01); *B01D 61/145* (2013.01); *B01D 61/422* (2013.01); *B01D 2257/60* (2013.01); *C01B 2203/0435* (2013.01)

(58) Field of Classification Search
USPC ..................................................... 423/658.3
See application file for complete search history.

(56) References Cited

U.S. PATENT DOCUMENTS

| 2009/0186393 | A1 | 7/2009 | Baker |
| 2009/0280548 | A1 | 11/2009 | Yoshida |
| 2018/0105836 | A1 | 4/2018 | Sarma |

OTHER PUBLICATIONS

Jin-Sook et al. "Comparison of Hydrogenases from *Clostridium butyricum* and Thiocapsaroseopersicina: Hydrogenases of *C. butyricum* and *T. roseopersicina*" Journal of Microbiology and Biotechnology, vol. 16 Issue 8 (2006): pp. 1210-1215; entire document, but especially: abstract, p. 1214 col 2 para 2, fig. 5.
PCT/US18/37167—WIPO—International Search Report—Dec. 20, 2018.
PCT/US18/37167—WIPO—Written Opinion of the International Searching Authority—Dec. 20, 2018.

* cited by examiner

SYSTEM AND METHODS FOR THE PRODUCTION OF HYDROGEN GAS

CROSS-REFERENCES TO RELATED APPLICATIONS

This application claims priority from PCT/US18/37167 filed Jun. 12, 2018, which claims the benefit of provisional U.S. Application No. 62/518,771, filed Jun. 13, 2017, which is incorporated by reference in its entirety.

TECHNICAL FIELD

This disclosure relates to industrial waste, and more particularly to systems and methods for using industrial waste for the production of hydrogen gas.

BACKGROUND

The statements in this section merely provide background information related to the present disclosure and may not constitute prior art.

Fuel cell electric vehicles offer a carbon emission free alternative to internal combustion engine powered vehicles. They use oxygen from air and hydrogen gas to generate an electric current with water vapor and heat as the byproducts. Hydrogen combustion gives a heat quantity per unit mass three times or greater than petroleum oils, and when supplied to fuel cells, can be converted into electric and thermal energies with a high degree of efficiency. Hence, hydrogen is a desirable resource.

Many automotive manufacturers also want the production of hydrogen to be renewable such that the end-to-end delivery (production through consumption) is clean and without CO2 emissions anywhere, "well to wheels". Hydrogen is the "currency" of all fuels, so its green production has beneficial applicability to all fuels, hydrocarbons, and chemicals that contain it.

Hydrogen, in its most common isotope, is the simplest of elements containing only one electron and one proton. Hydrogen is one of the most abundant elements on Earth, found in ubiquitous compounds such as water and hydrocarbons. However, hydrogen gas, which exists in diatomic form as H2 under normal conditions, rarely exists in Earth's atmosphere or elsewhere on Earth.

The production of H2 gas can be accomplished in several ways and from several precursors. However, with the exception of electrolysis using solar, wind or hydroelectric power, all current commercial processes to produce H2 gas result in carbon emissions into the atmosphere and consume more energy in the process than the resulting H2 gas contains.

Further, treatment and reduction of concentrations of pollutants in industrial waste sources to environmentally acceptable levels is a long standing environmental and economic problem. It is important to be able to treat such wastes and remove metals, hazardous materials, and toxic substances, with minimal amounts of solid wastes remaining in a cost-effective manner. The ultimate solution to such environmental problems, recovery, recycling, and reuse of metals contained within waste sources has been inadequately addressed.

Hydrogenase enzymes catalyze the production of H2 gas from protons and electrons. Although protons and electrons do not exist separate from the atoms they constitute, electron sources are readily available and electrons can easily be focused to a hydrogenase catalyzed reaction through many well-documented methods. For most compounds, it requires significant cost to separate protons from their various compounds or to generate constituent compounds.

Therefore, a need exists for an environmental and economic method and system for cleaning up industrial waste while producing hydrogen gas.

SUMMARY

Method and system is disclosed for producing hydrogen gas using industrial waste catalyzed with hydrogenase.

Method and system is disclosed for using industrial waste for the production of hydrogen gas. The method includes examining a ph level of the industrial waste, identifying and removing contaminate from the industrial waste, conditioning the industrial waste, using the proton-rich solution in conjunction with an electron source in the presence of hydrogenase catalyst, removing hydrogen gas from the industrial waste, and storing the hydrogen gas.

Certain embodiments of the invention include applying the biological catalyst in vitro.

Certain embodiments of the invention include conditioning the industrial waste to a predefined acidic ph level, e.g., 3-7.8.

This summary is provided merely to introduce certain concepts and not to identify key or essential features of the claimed subject matter.

BRIEF DESCRIPTION OF THE DRAWINGS

One or more embodiments will now be described, by way of example, with reference to the accompanying drawings, in which.

DETAILED DESCRIPTION

Figure 1:
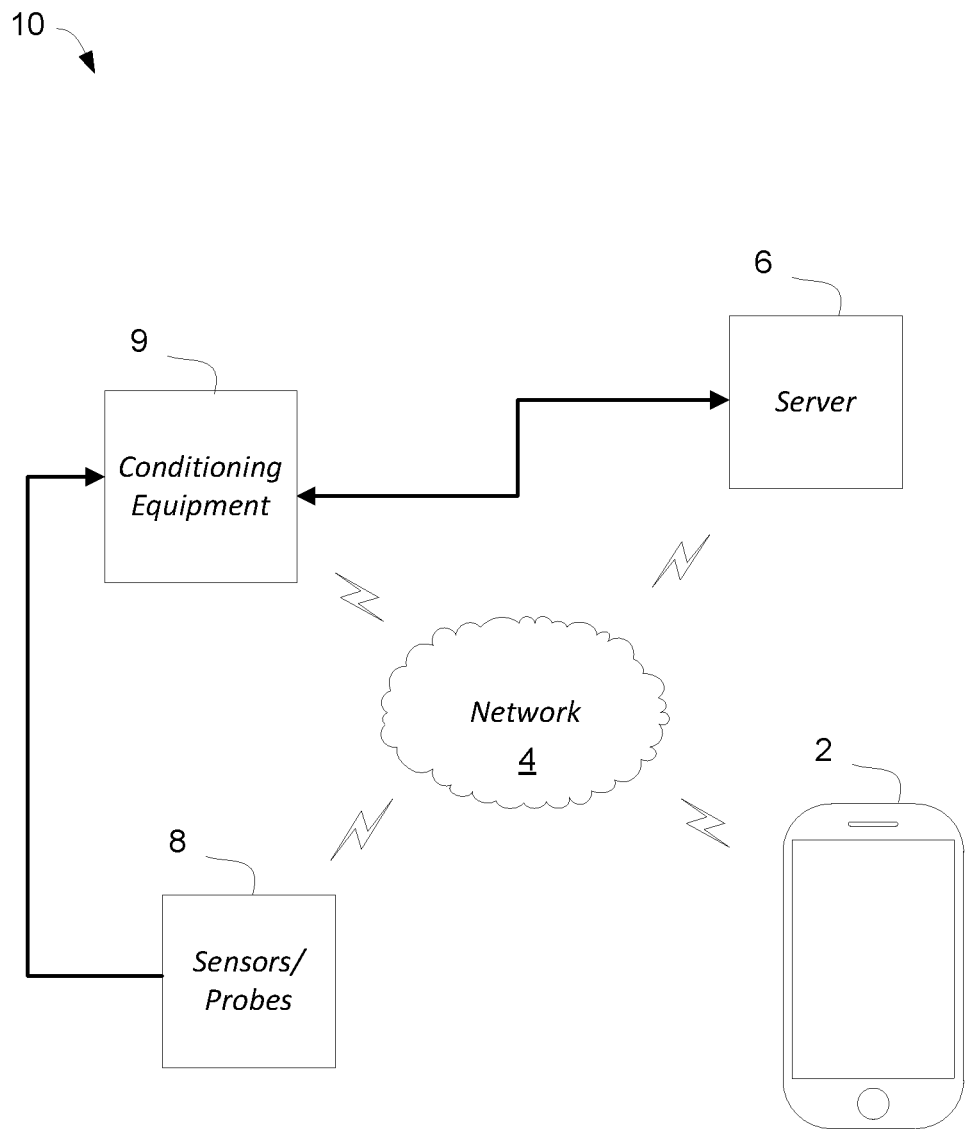
FIG. 1 schematically shows an exemplary hydrogen production system, in accordance with the present disclosure.

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

As used in the description herein and throughout the claims, the following terms take the meanings explicitly associated herein, unless the context clearly dictates otherwise: the meaning of "a," "an," and "the" includes plural reference, the meaning of "in" includes "in" and "on." The term "based upon" is not exclusive and allows for being based on additional factors not described, unless the context clearly dictates otherwise. Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner.

Referring now to the drawings, wherein the depictions are for the purpose of illustrating certain exemplary embodiments only and not for the purpose of limiting the same, FIG. 1 schematically shows an exemplary hydrogen production system 10 that may help implement the methodologies of the present disclosure. The system 10 includes a server system 6, a network 4, and a mobile device 2. In various embodiments, one or more types of conditioning equipment 9 may be communicatively connected to the system 10. In various embodiments, the system 10 is not adapted for communication with the mobile device 2. In Various embodiments, the various components may be directly communicatively connected and/or connected through the network 4. The various components may be physically connected to the network 4 during selected periods of operation without departing from the teachings herein.

Components of the system 10 are shown in FIG. 1 as single elements. Such illustration is for ease of description and it should be recognized that the system 10 may include multiple additional devices, sensors, probes, conditioning equipment, etc. It is to be understood that the system 10 may include a number of other devices, components, modules, and the like. It is to be understood and appreciated that, the various systems may include additional devices, components, modules, and so on, and/or may not include all of the devices, components, modules and so on, discussed in connection with the figures. A combination of these approaches may also be used.

The network 4 may be any suitable series of points or nodes interconnected by communication paths. The network 4 may be interconnected with other networks and contain sub networks network such as, for example, a publicly accessible distributed network like the Internet or other telecommunications networks (e.g., cellular network, intranets, virtual nets, overlay networks and the like). The network 4 may facilitates the exchange of data between and among the mobile device 2, the server system 6, the conditioning equipment 9, and/or one or more sensors or probes. In various embodiments the conditioning equipment 9 and sensors/probes 8 can be directly connected to the server 6.

The server system 6 may be a computer including high-speed microcomputers, minicomputers, mainframes, and/or data storage devices. The server system 6 preferably executes database functions including storing and maintaining a database and processes requests from a user, administrator or from a user or administrator via the mobile device 2 to extract data from, or update, a database as described herein below. The server 6 may additionally provide processing functions for the mobile device 2 as will become apparent to those skilled in the art upon a careful reading of the teachings herein.

In addition, the mobile device 2 may include one or more applications that the user may operate. Operation may include downloading, installing, turning on, unlocking, activating, or otherwise using an application. The application may comprise at least one of an algorithm, software, computer code, and/or the like, for example, mobile application software. In the alternative, the application may be a website accessible through the world wide web.

Figure 2:
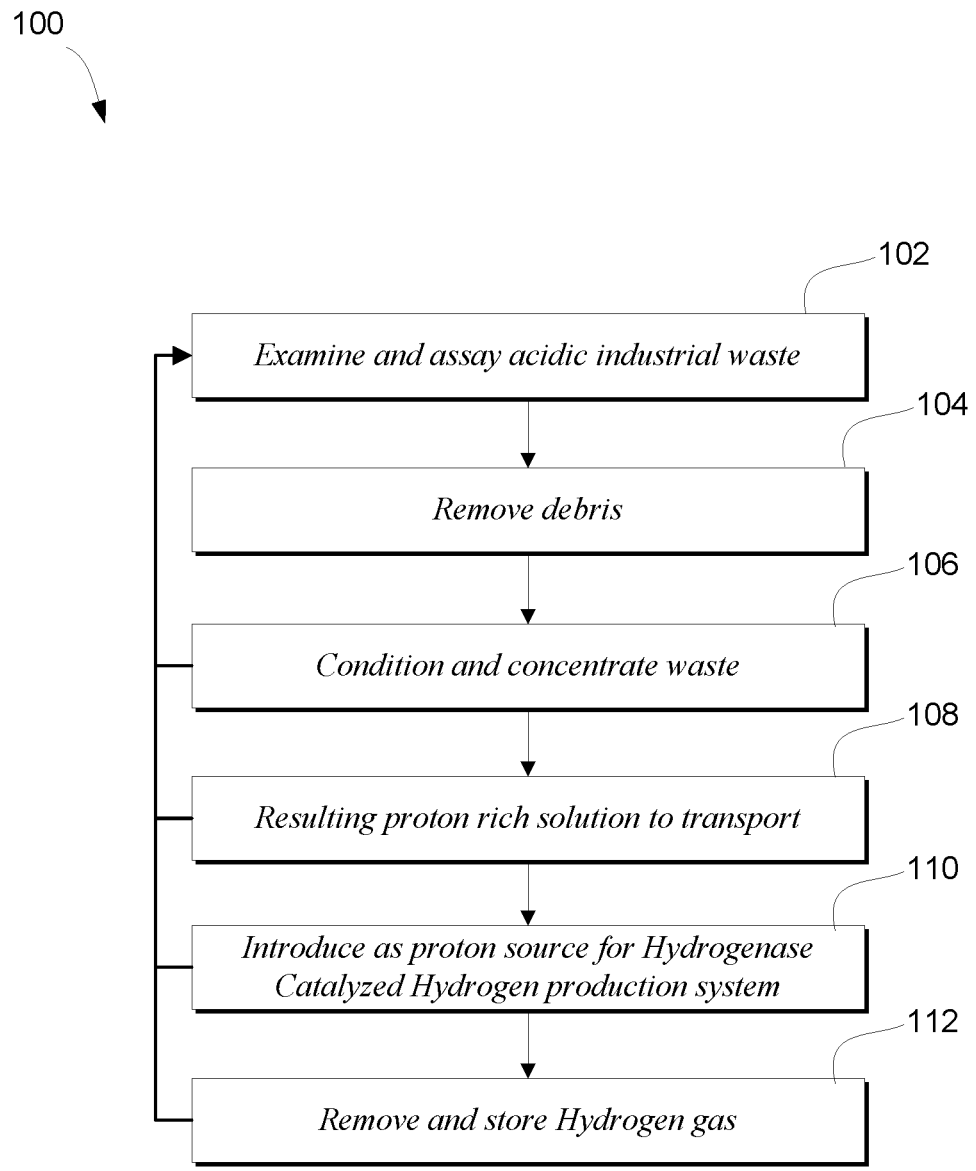
FIG. 2 show a process for using industrial waste for the production of hydrogen gas, in accordance with the present disclosure.

FIG. 2 shows an exemplary process 100 for using industrial waste for the production of hydrogen gas. The process 100 may be executed by the server 6. The process 100 begins at step 102, where an industrial waste site is examined for preferential conditions. The preferential conditions may include one or more criterion including, e.g.,: (1) a predefined ph level as effected by economics; (2) a predefined water concentration; (3) radiation below a threshold, any compounds which are not removable by technologies or methods suggested herein and which have been shown to reduce or eliminate the ability of hydrogenase to act as a catalysis for forming H2 from protons and electrons.

In the world, acidic industrial waste streams, including acidic mine drainage, may provide a potential source of protons for hydrogen production. Many iron, steel and metal production processes result in acidic waste as does plating and other finishing processes. Acidic waste is also common as a result of both metal mining of sulfide ores of cooper, zinc, lead, silver and other metals and coal mining. Any industrial waste which has a low pH (<7) might be a viable source of protons.

After examining the site, debris and contaminate is removed from the waste at step 104. Debris can be removed using one or more known tools and techniques including screening, filtering, etc. Known valuable materials may be extracted from the waste at this step. For example, precious metals such as Au, Ag, Zn, Fe, Ca, Cu, Ni, Ti may be removed, when economically practical. In some waste sites, organic waste may be physically removed. In some waste sites, metals may be captured from water by immobilize them in a sludge, coagulating and separating the sludge from the water, de-watering the sludge and burning off the organic matter, and recovering selected metal values by inorganic metal-winning process steps, as is known in the art.

After debris removal, the waste may be conditioned and concentrated at step 106. Conditioning may include one or more known techniques including membrane filtration, reverse osmosis, electro dialysis, nanofiltration, centrifuge, and/or concentration of material. While conditioned, the sensors and probes may be programmed to concurrently and/or intermittently monitor conditions of the waste for reporting and analysis. In one embodiment, waste is conditioned until reaching a predefined threshold of material concentration. In one embodiment, waste is conditioned for a predefined time. In one embodiment, waste is conditioned for a predefined number of operational cycles, e.g., one cycle of operational cycle of electro dialysis, one cycle of material concentration. In one embodiment, the material is conditioned to be a proton-rich solution. In one embodiment, the waste is concentrated to a predefined ph level. In one embodiment, the ph level is defined as 6.5 or lower. In one embodiment, the ph level is defined as 6.5. In one embodiment, the ph level is concentrated to a range of between 3-7. Common conditioning techniques have issues in terms of cost, efficacy and thoroughness or remediation, which may be considered when selecting an industrial waste site for application of the disclosure herein.

After conditioning and concentrating the waste, the resulting proton-rich solution is ready for transport at step 108. Transport may be executed via a piping system or transport may be executed from the site via vehicles or by rail. At step 110, the resulting proton rich-solution is used as the proton source in a hydrogenase catalyzed hydrogen production system. In one embodiment, an electron source is applied to the solution, which may be supplied by a power source, e.g., a battery, conventional electrical outlet, solar panels, etc.

The biological catalyst in some embodiments is hydrogenase. In one embodiment, the biological catalyst is applied in vitro.

When the conditioned acidic industrial waste, H+ ions are available for reactions. Acidic compounds exist within the industrial waste, by definition and depending on their strength (i.e., pH), have an abundance of protons which can be utilized and combined with the supplied electrons to produce H2 gas.

After and/or while applying the biological catalyst, hydrogen gas may be extracted and stored at step 112. Extraction may be made by a hydrogen collection system, which may be a vacuum. Storage may be accomplished as a simple pressurized gas or liquid. Or it may be stored in a hydrogen absorbing compound, e.g., a metal hydride.

The schematic flow chart diagrams included herein are generally set forth as logical flow chart diagrams. As such, the depicted order and labeled steps are indicative of one embodiment of the presented process. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the process. For example, an arrow may indicate a waiting or monitoring period of unspecified duration between enumerated steps of the depicted process. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Additionally, the order in which a particular method occurs may or may not strictly adhere to the order of the corresponding steps shown. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures. For example, steps 102, 104, 106 and 110 may be executed concurrently in some embodiments.

Additionally, examples in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing.

As will be appreciated by one skilled in the art, aspects of the present disclosure may be embodied as a system, method, and/or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present disclosure may take the form of a computer program product embodied in one or more computer readable medium(s) having program code embodied thereon.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

The computer readable program code may be stored and/or propagated on in one or more computer readable medium(s). The computer readable medium may be a tangible computer readable storage medium storing the computer readable program code, such storing is known in the art. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium.

In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The computer readable program code may execute entirely on the server 6, partly on the server 6, partly on the mobile device 2 and partly on the server 6 or entirely on the mobile device 2.

While the foregoing disclosure discusses illustrative embodiments, it should be noted that various changes and modifications could be made herein without departing from the scope of the described embodiments as defined by the appended claims. Accordingly, the described embodiments are intended to embrace all such alterations, modifications and variations that fall within scope of the appended claims. Furthermore, although elements of the described embodiments may be described or claimed in the singular, the plural is contemplated unless limitation to the singular is explicitly stated. Additionally, all or a portion of any embodiment may be utilized with all or a portion of any other embodiments, unless stated otherwise.

The invention claimed is:

1. A method of using an acidic industrial waste as a source of protons for production of hydrogen gas, the method comprising:
   removing organic matter from the acidic industrial waste, the acidic industrial waste being metal-based;
   forming a proton-rich solution by conditioning and concentrating the acidic industrial waste;
   supplying electrons by applying an electron source to the proton-rich solution; and
   using the resulting proton rich solution as a proton source, the supplied electrons as an electron source to be combined with protons of the proton source, and hydrogenase as a catalyst to produce the hydrogen gas.

2. The method of claim 1, further comprising removing one or more metals from the acidic industrial waste.

3. The method of claim 1, further comprising removing one or more of Au, Ag, Zn, Fe, Ca, Cu, Ni, Ti from the acidic industrial waste.

4. The method of claim 1, wherein the conditioning comprises processing the acidic industrial waste through a membrane filtration system.

5. The method of claim 1, wherein the conditioning comprises reverse osmosis.

6. The method of claim 1, wherein conditioning comprises electro dialysis.

7. The method of claim 1, wherein the conditioning comprises concentrating the acidic industrial waste to pH of less than 6.5.

8. The method of claim 1, further comprising examining the acidic industrial waste for one or more conditions at an industrial waste site.

9. The method of claim 8, wherein the examining is executed by a server system.

10. The method of claim 8, further comprising transporting the proton-rich solution from the industrial waste site before applying the electron source.

11. The method of claim 1, further comprising storing the produced hydrogen gas in a hydrogen absorbing compound.

12. A method for using an acidic industrial waste for production of hydrogen gas, the method comprising:
    examining the acidic industrial waste for one or more conditions at an industrial waste site;
    removing contaminate and organic matter from the acidic industrial waste;
    concentrating and conditioning the acidic industrial waste to a predefined pH of 6.5 or below to form a proton-rich solution; and
    using the resulting proton rich solution as a proton source in a biologically catalyzed hydrogen production system to produce the hydrogen gas.

13. The method of claim 12, wherein the acidic industrial waste is a metal-containing industrial waste.

14. The method of claim 12, further comprising supplying electrons by applying an electron source to the proton-rich solution.

15. The method of claim 12, wherein the biological catalyst is hydrogenase.

16. The method of claim 12, wherein the concentrating and conditioning are performed at the industrial waste site.

17. The method of claim 12, further comprising transporting the proton-rich solution from the industrial waste site to the biologically catalyzed hydrogen production system.

18. The method of claim 12, wherein the one or more conditions include a predefined pH, a predefined water concentration, and/or radiation below a threshold.

* * * * *